US010935509B2

(12) United States Patent
Liu et al.

(10) Patent No.: US 10,935,509 B2
(45) Date of Patent: Mar. 2, 2021

(54) GAS SENSING METHOD WITH CHEMICAL AND THERMAL CONDUCTIVITY SENSING

(71) Applicant: INVENSENSE, INC., San Jose, CA (US)

(72) Inventors: Fang Liu, San Jose, CA (US); Peter Hartwell, Menlo Park, CA (US); Martin Lim, San Mateo, CA (US); Yushi Yang, Singapore (SG)

(73) Assignee: INVENSENSE, INC., San Jose, CA (US)

( * ) Notice: Subject to any disclaimer, the term of this patent is extended or adjusted under 35 U.S.C. 154(b) by 0 days.

(21) Appl. No.: 16/786,361

(22) Filed: Feb. 10, 2020

(65) Prior Publication Data

US 2020/0173946 A1     Jun. 4, 2020

Related U.S. Application Data

(62) Division of application No. 15/484,864, filed on Apr. 11, 2017, now Pat. No. 10,598,621.

(51) Int. Cl.
    *G01N 27/04*     (2006.01)
    *G01N 27/18*     (2006.01)
    *G01N 27/12*     (2006.01)
    *G01N 33/00*     (2006.01)

(52) U.S. Cl.
    CPC ........... *G01N 27/04* (2013.01); *G01N 27/123* (2013.01); *G01N 27/18* (2013.01); *G01N 33/0073* (2013.01); *G01N 27/128* (2013.01); *G01N 33/004* (2013.01)

(58) Field of Classification Search
    CPC ........... G01N 27/4163; G01N 33/0006; G01N 27/04; G01N 27/046; G01N 27/123; G01N 27/125; G01N 27/18; G01N 27/4141; G01N 27/4148; G01N 33/0036; G01N 27/124
    See application file for complete search history.

(56) References Cited

U.S. PATENT DOCUMENTS

| 6,902,701 B1* | 6/2005 | Hughes | G01N 1/405 |
| | | | 29/592 |
| 2014/0020448 A1* | 1/2014 | Matsukura | G01N 33/0036 |
| | | | 73/25.01 |
| 2017/0160250 A1* | 6/2017 | Savoy | G01N 27/125 |
| 2018/0003660 A1* | 1/2018 | Tayebi | G01N 33/0006 |

* cited by examiner

*Primary Examiner* — Tung X Nguyen
*Assistant Examiner* — Feba Pothen
(74) *Attorney, Agent, or Firm* — Amin, Turocy & Watson, LLP

(57) ABSTRACT

The present invention relates to methods for detecting gases in an environment using chemical and thermal sensing. In one embodiment, a method includes exposing a chemiresistor embedded within a sensor pixel to a gas in an environment; setting a heater embedded within the sensor pixel to a sensing temperature, the sensing temperature being greater than room temperature; measuring an electrical resistance of the chemiresistor in response to setting the heater to the sensing temperature; and in response to a difference between the electrical resistance of the chemiresistor and a reference electrical resistance being less than a threshold, supplying a fixed power input to the heater embedded within the sensor pixel and measuring a temperature of the sensor pixel relative to a reference temperature.

12 Claims, 14 Drawing Sheets

GAS SENSING METHOD WITH CHEMICAL AND THERMAL CONDUCTIVITY SENSING

CROSS-REFERENCE TO RELATED APPLICATION

This patent application is a divisional application of, and claims priority to, U.S. patent application Ser. No. 15/484,864, filed on Apr. 11, 2017, and entitled "GAS SENSING DEVICE WITH CHEMICAL AND THERMAL CONDUCTIVITY SENSING," the entirety of which is incorporated by reference herein.

BACKGROUND

Certain gas sensors leverage physical or chemical changes in a chemical sensing material, e.g., a chemiresistor material, while in the presence of a gas to determine the concentration of that gas in the surrounding environment. However, chemiresistor-based gas sensors cannot sense inert gases, such as carbon dioxide or nitrogen, due to reaction limitations of metal-oxide-semiconductor (MOS) structures. Accordingly, it would be desirable to implement gas sensor devices that can detect a wider variety of gases.

SUMMARY

The following presents a simplified summary of one or more of the embodiments of the present invention in order to provide a basic understanding the embodiments. This summary is not an extensive overview of the embodiments described herein. It is intended to neither identify key or critical elements of the embodiments nor delineate any scope of embodiments or the claims. This Summary's sole purpose is to present some concepts of the embodiments in a simplified form as a prelude to the more detailed description that is presented later. It will also be appreciated that the detailed description may include additional or alternative embodiments beyond those described in the Summary section.

The present disclosure recognizes and addresses, in at least certain embodiments, the issue of detecting reactive as well as inert and/or other nonreactive gases. The disclosed gas sensor uses a thermal conductivity sensing method in addition to a chemiresistor-based sensing method in order to sense a broader range of gases using a single gas sensing platform. The disclosed gas sensor combines chemiresistor sensing and thermal conductivity sensing in the same device, thereby improving gas sensing species range while reducing the number of gas sensor devices and/or other related equipment.

In one aspect disclosed herein, a method includes exposing a chemiresistor embedded within a sensor pixel to a gas in an environment, setting a heater embedded within the sensor pixel to a sensing temperature, the sensing temperature being greater than room temperature, measuring an electrical resistance of the chemiresistor in response to setting the heater to the sensing temperature, and, in response to a difference between the electrical resistance of the chemiresistor and a reference electrical resistance being less than a threshold, supplying a fixed power input to the heater embedded within the sensor pixel and measuring a temperature of the sensor pixel relative to a reference temperature.

Other embodiments and various examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

DETAILED DESCRIPTION

The disclosure recognizes and addresses, in at least certain embodiments, the issue of detecting reactive as well as inert and/or other nonreactive gases. The disclosed gas sensor uses a thermal conductivity sensing method in addition to a chemiresistor-based sensing method in order to sense a broader range of gases using a single gas sensing platform. The disclosed gas sensor combines chemiresistor sensing and thermal conductivity sensing in the same device, thereby improving gas sensing species range while reducing the number of gas sensor devices and/or other related equipment.

When compared to conventional technologies, the gas sensor of the disclosure can detect a wide variety of gases using a single sensor device, with associated lower costs, complexity, etc., that would result from utilizing multiple sensor devices. Moreover, the gas sensor of the disclosure can be configured to utilize thermal conductivity sensing specifically in the presence of an inert gas (and to not utilize thermal conductivity sensing in the absence of an inert gas), which can result in greater efficiency and/or performance, lower power usage, etc., for some applications.

Figure 1:
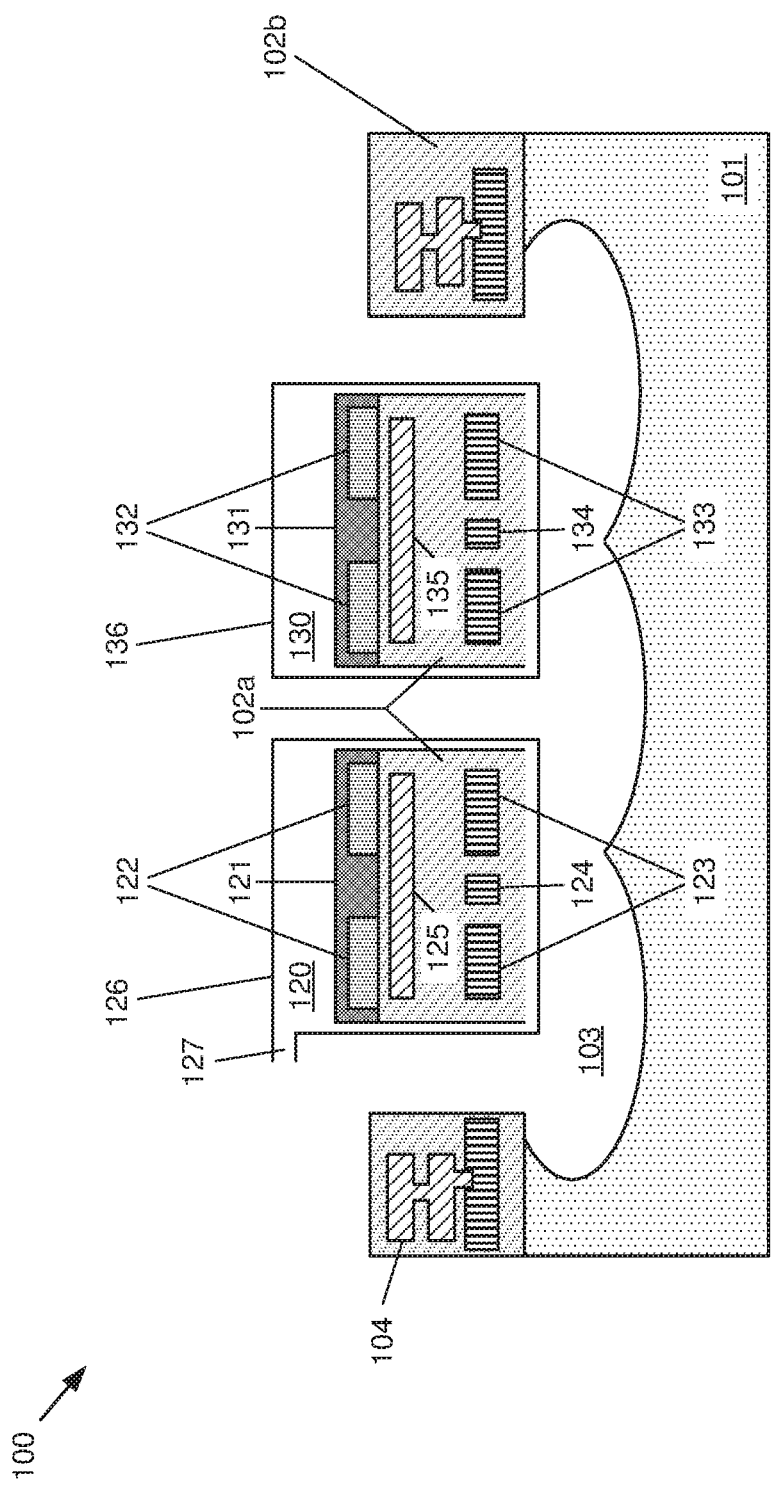
FIG. 1 depicts a cross sectional side view of an example of a gas sensor in accordance with one or more embodiments of the disclosure.

With reference to the drawings, FIG. 1 depicts a side cross section view of an example of a gas sensor 100 in accordance with one or more embodiments of the disclosure. As illustrated, the gas sensor includes a substrate 101 on which the other elements are built. On the substrate 101, a dielectric layer 102 is deposited or formed. Here, the gas sensor 100 includes a sensor pixel 120 and a temperature reference structure (TRS) 130. Pixel 120 is configured for sensing a gas in a surrounding environment in accordance with various aspects described herein, and TRS 130 is configured to provide a temperature reference for the gas sensor 100 in association with thermal conductivity sensing. While TRS 130 is illustrated in FIG. 1 and described in various embodiments herein as a separate sensor pixel, it should be appreciated that TRS 130 could be any suitable structure(s) adapted to provide a temperature reference for the gas sensor 100, and may include any such structure(s) in addition to, or in place of, a sensor pixel. Together, pixel 120 and TRS 130 can be used together to detect gases in a surrounding environment according to both chemiresistor-based sensing and thermal conductivity sensing as described herein, thereby enabling the sensor to detect numerous different gases at various concentrations. In an aspect, the gas sensor 100 can be constructed using micro-electrical-mechanical systems (MEMS) in a composite metal-oxide-semiconductor (CMOS) process as described below.

As shown in FIG. 1, pixel 120 includes a chemical sensing element 121 composed of a chemical sensing material, and TRS 130 includes a chemical sensing element 131 composed of similar or different chemical sensing material. Chemi-sensitive materials utilized in the chemical sensing elements 121, 131 may be metal oxides including oxides of chromium, manganese, nickel, copper, tin, indium, tungsten, titanium, vanadium, iron, germanium, niobium, molybdenum, tantalum, lanthanum, cerium, and/or neodymium. Alternatively, these materials may be composite oxides including binary, ternary, quaternary and/or complex metal oxides. Metal oxide gas sensors are low cost and have flexibility in production, are simple to use, and have a large number of detectable gases/possible application fields. Accordingly, the metal oxide used in a specific application may be selected for sensitivities to certain chemicals. Metal oxides also function well as a chemical sensing material because they can be used to detect chemical changes through conductivity change as well as by measuring the change of capacitance, work function, mass, optical characteristics or reaction energy. In one example, the chemical sensing elements 121, 131 function as chemiresistors such that an electrical resistance of the chemical sensing elements 121, 131 change based on the chemical properties of gases or other chemicals that come into contact with the chemical sensing elements 121, 131.

Adjacent to the chemical sensing elements 121, 131, there are contact electrodes 122, 132. The contact electrodes are electrically connected to the chemical sensing elements 121, 131 and are used to detect changes in the chemical sensing elements 121, 131 as the concentration of the target gas changes. The contact electrodes 122, 132 can be made of conductive materials including noble metals, titanium nitride, polysilicon, and/or tungsten.

Pixel 130 and TRS 130 also include respective heating elements 123, 133. The heating elements 123, 133 can be formed through standard CMOS processes to form a resistive heating element, including by using polysilicon, tungsten, titanium nitride, or silicon carbide. In one embodiment of the gas sensor, the heating elements 123, 133 are formed based on processes that optimize device surface area and improve heating efficiency. In an aspect, the heating elements 123, 133 may only be sufficiently sensitive at a high temperature. For example, the operating temperature of some chemical sensing material is ideally above 100 degrees Celsius to achieve sensitivity sufficient for robust measurement. Moreover, different chemical sensing materials may have different activation temperatures, and the heating element can be used to optimize conditions for a given gas.

Pixel 120 and TRS 130 also include respective temperature sensors 124, 134 to measure the temperature of pixel 120 and TRS 130 and provide feedback for temperature control. The temperature sensors 124, 134 may be formed from substantially the same material and at substantially the same time as the heating elements 123, 133, thereby reducing processing time and complexity. For example, the temperature sensors 124, 134 can be implemented with the heating elements 123, 133 in the same film deposition process. Film of the film deposition process can be, for example, polycrystalline silicon with different doping levels and/or metal silicide.

In an aspect, the temperature sensors 124, 134 may be formed from a material having an electrical resistance that changes as a function of temperature. For example, the following equation demonstrates a relationship between resistance and temperature change for a conductive material. In the equation below, $R_{h/t}(T)$ is the resistance of the material at the current temperature T. $R(T_0)$ is the resistance of the material at an initial temperature $T_0$ and $\alpha$ is the temperature coefficient of resistivity of the material.

$$R_{h/t}(T)=R(T_0)[1+\alpha(T-T_0)]$$

As further shown in FIG. 1, a dielectric layer 102a-b is adjacent to the chemical sensing element 121, 131, contact electrodes 122, 132, heating elements 123, 133, and temperature sensors 124, 134. The dielectric layer 102a-b provides thermal coupling between the heating elements 123, 133 and the chemical sensing element 121, 131 so that the heat provided by the heating elements 123, 133 is conducted to the chemical sensing element 121, 131. Accordingly, the dielectric layer 102a-b is preferably composed, at least in part, by a low-k dielectric material with a given thermal conductivity.

The dielectric layer 102a provides mechanical support for the elements of pixel 120 and TRS 130. At locations not shown in FIG. 1, the dielectric layer 102b from the bulk of the chip is connected to the dielectric layer 102a in the pixel 120 and TRS 130. These connections provide mechanical support and allow for electrical connections to the contact electrodes 122, 132, heating elements 123, 133, and temperature sensors 124, 134.

In one example, the heating elements 123, 133 are implemented as microheaters. The temperature sensors 124, 134 can be employed to sense temperature of the respective heating elements 123, 133 (e.g., the microheaters). As such, the temperature sensors 124, 134 and the heating elements 123, 133 can be implemented separate from the CMOS substrate layer 101 for improved thermal isolation (e.g., a micro-bridge structure associated with the heating elements 123, 133 can be outside of the CMOS substrate layer 101 for improved thermal isolation). In a non-limiting example, a thickness of the dielectric layer 102a-b can be approximately equal to 10 microns. However, it is to be appreciated that the dielectric layer 104 can be of a different thickness.

As further shown in FIG. 1, a portion of the substrate 101 underneath pixel 120 and TRS 130 is etched or otherwise removed to create a thermal isolation cavity 103 that thermally isolates pixel 120 and TRS 130 from the bulk of the substrate. The thermal isolation cavity 103 allows integration of the chemical sensor with other devices (e.g., an application-specific integrated circuit (ASIC) 104) on the same chip. The thermal isolation cavity 103 protects other devices on the chip from heat produced by the heating elements 123, 133. This, in turn, protects the other devices from possible thermal damage and reduces the power consumption associated with heating pixel 120 and TRS 130 to an operating temperature since less heat is dissipated from the pixel 120, 130 to the bulk substrate. The chemical sensing elements 121, 131 may have an operating or activation temperature at which, or above which, the sensitivity of the chemical sensing elements 121, 131 reaches a desired threshold.

As additionally shown in FIG. 1, the heating elements 123, 133 and temperature sensors 124, 134 are electrically and/or thermally coupled to respective heat transfer layers 125, 135. The heat transfer layers 125, 135 can be associated with a set of metal interconnections (e.g., a set of metal vias). For example, the heat transfer layers 125, 135 can respectively comprise sets of metal interconnections that include aluminum, tungsten or another type of metal. Furthermore, the heat transfer layers 125, 135 can respectively include a plurality of metal layers that are electrically coupled via the set of metal interconnections. In an implementation, the heating elements 123, 133, temperature sensors 124, 134, and/or the heat transfer layers 125, 135 can be suspended in the dielectric layer 102a. For example, the heating elements 123, 133, temperature sensors 124, 134, and/or the heat transfer layers 125, 135 can be surrounded by a dielectric material of the dielectric layer 102a. As such, both in-plane temperature uniformity and out-of-plane temperature uniformity can be achieved for the gas sensor device 100.

In an embodiment, pixel 120 and TRS 130 are encapsulated via respective chambers or chamber structures 126, 136. The chambers 126, 136 are constructed of a gas-impermeable material that regulate and/or restrict the flow of gases into and/or out of an area associated with pixel 120 and/or TRS 130. Here, chamber structure 126 is fitted with a vent 127 to enable one or more gases in the environment surrounding the gas sensor 100 to enter the chamber 126 and be detected by pixel 120. In contrast, chamber 136 forms an impermeable seal or barrier between TRS 130 and the environment, thereby preventing the escape of a reference gas and/or otherwise reducing outside influence on the reference temperature. Various operating principles for TRS 130 are described in further detail below.

In another embodiment, the gas sensor 100 includes one or more ASICs 104 or other suitable controllers. As shown in FIG. 1, ASIC 104 can be fabricated in the dielectric layer 102b. Both the dielectric layer 102b and the ASIC 104 can be deposited or formed on the CMOS substrate layer 101. The ASIC 104 can be mechanically coupled to the CMOS substrate layer 101. It is to be appreciated that the ASIC 104 can comprise one or more ASIC devices.

ASIC 104 can be configured for controlling heating of the heating elements 123, 133, evaluating temperature and/or determining concentrations of chemicals associated with the chemical sensing elements 121, 131, etc. In an implementation, ASIC 104 can include integrated circuitry configured to supply an electrical current to the heating elements 123, 133 (e.g., so that heating elements 123, 133 can generate an amount of heat based on the electrical current supplied by ASIC 104). In one example, ASIC 104 can be a heater control circuit. In another implementation, ASIC 104 can include integrated circuitry configured to control an operational temperature of the heating elements 123, 133. In yet another implementation, ASIC 104 can include integrated circuitry configured to measure changes associated with the chemical sensing elements 121, 131 (e.g., by measuring electrical resistance of the chemical sensing elements 121, 131, etc.). In an example, ASIC 104 is electrically coupled to one or more of the contact electrodes 122, 132.

Figure 2:
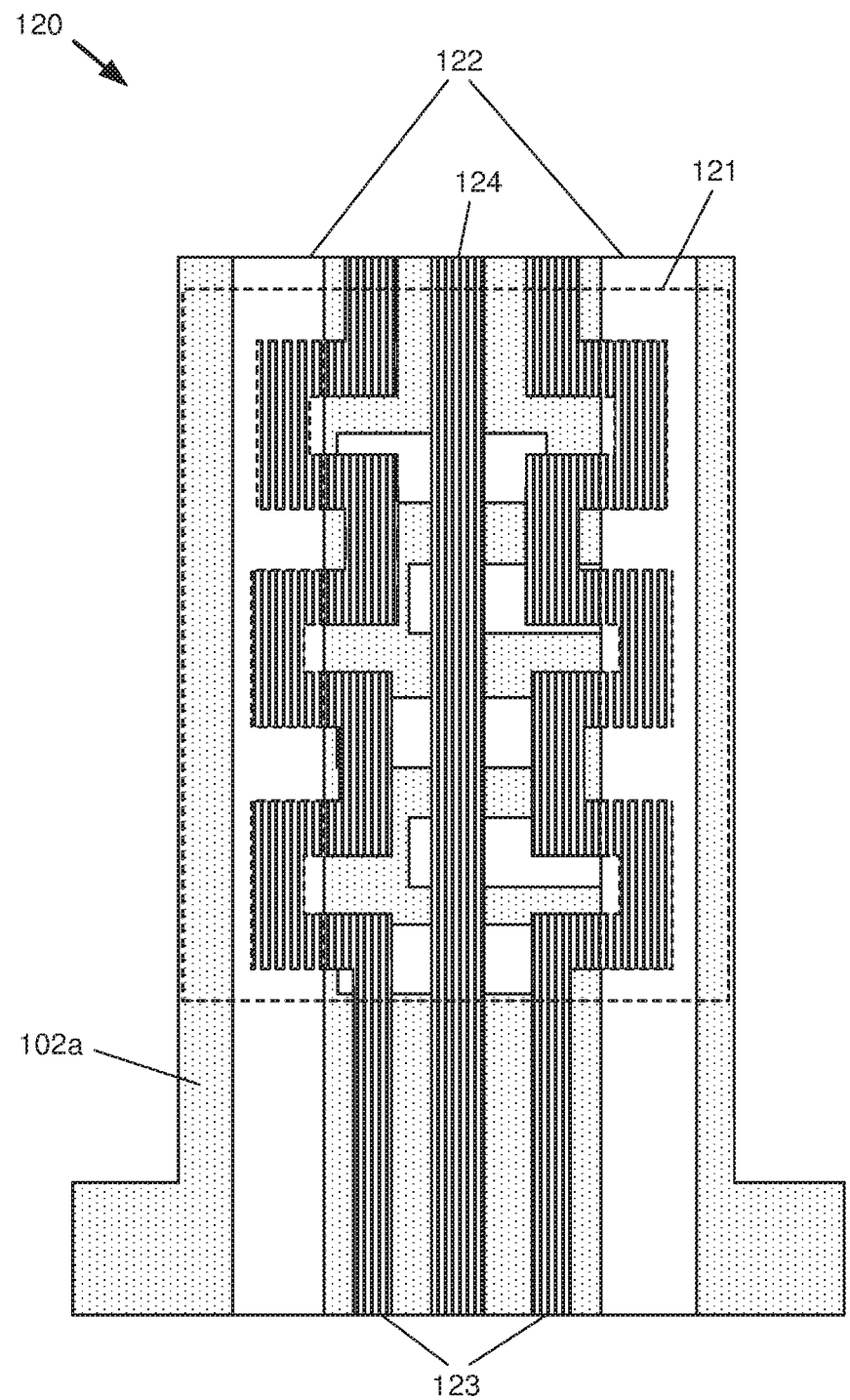
FIG. 2 depicts a top down view of a portion of the example gas sensor of FIG. 1.

FIG. 2 is a top-down view of the pixel 120 of the gas sensor 100 in FIG. 1. The pixel 120 includes the chemical sensing element 121, which is depicted in FIG. 2 by a region delimited by a dotted line. Adjacent to the chemical sensing element 121 there are contact electrodes 122. The contact electrodes are electrically connected to the chemical sensing element 121 and are used to detect changes in the chemical sensing element 121 as the concentration of the target gas changes. The pixel 120 also includes a heating element 123. As shown in FIG. 2, the heating element 123 may have a serpentine structure to increase the surface area and heating efficiency of the heating element 123. The pixel 120 further includes a temperature sensor 124 to measure the temperature of the pixel 120 and provide feedback for temperature control. In the pixel 120, the dielectric layer 102a is adjacent to the chemical sensing element 121, contact electrodes 122, heating element 123, and temperature sensor 124.

As described above, in one embodiment, the gas sensor includes heating elements 123, 133 embedded in a suspended structure overlying a doped semiconductor substrate 101. The heating elements 123, 133 are configured to generate an amount of heat to bring the chemical sensing elements 122, 132 to an operating temperature. The chemical sensing elements 122, 132 are thermally coupled to the heating element 123, 133. Further, the chemical sensing element 122 of pixel 120 is exposed to an environment, via the vent 127 of chamber 126, which contains the gas to be measured.

In one embodiment, the chemical sensing element 122 of pixel 120 comprises a metal oxide compound having an electrical resistance based on the concentration of a gas in the environment and the operating temperature of the chemical sensing element 122. In this embodiment, the operating temperature of the chemical sensing element 122 is greater than room temperature and determined by the amount of heat generated by the heating element 123. In one example the operating temperature of the chemical sensing element 122 is approximately 100 degrees Celsius.

In another embodiment, the gas sensor 100 includes temperature sensors 124, 134 configured to supply an electric signal in response to the temperature of the respective chemical sensing elements 122, 132. The temperature sensors 124, 134 are thermally coupled to the chemical sensing elements 122, 132 so that the temperature sensor 124, 134 can determine the temperature at the respective chemical sensing elements 122, 132. In one example, the temperature sensor 124, 134 comprise any one of polycrystalline silicon, tungsten, and/or titanium nitride.

Figure 3:
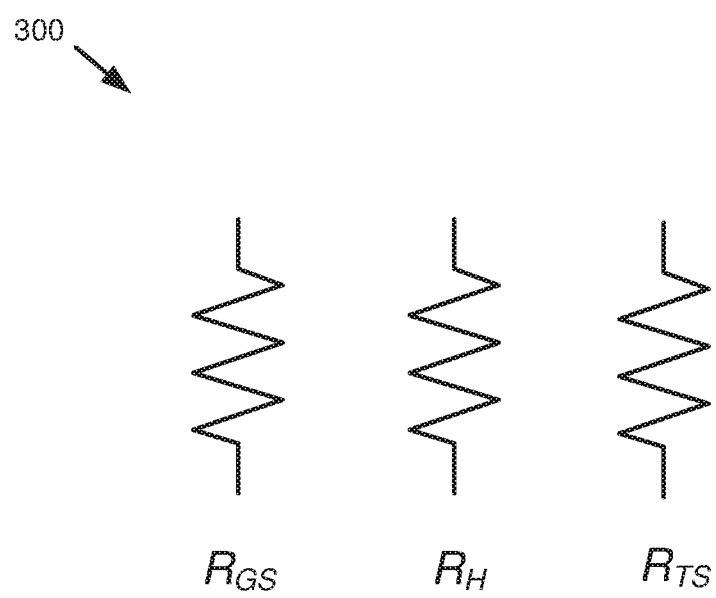
FIG. 3 is an equivalent schematic diagram representing the example gas sensor of FIGS. 1-2.

FIG. 3 depicts a schematic diagram 300 representing resistances associated with the sensor pixel 120. The schematic diagram 300 includes resistors $R_{GS}$, $R_H$, and $R_{TS}$, which correspond to the equivalent resistance of the chemical or gas sensing material 121, the heating element 123, and the temperature sensor 124, respectively. In one example, the chemical sensing element 131, heating element 133, and temperature sensor 134 of the TRS 130 can be implemented in a similar manner.

As shown in schematic diagram 300, the chemical sensing element 121, heating element 123, and temperature sensor 124 can be electrically connected in a parallel resistor configuration. In an aspect, the heating element 123 is a resistive heating element. For example, the heating element 123 can be implemented as a resistive structure to generate an amount of heat (e.g., an amount of heat for the chemical sensing element 121).

In an aspect, resistance of the heating elements 123, 133 can be tuned based on a geometry of the heating element 123, 133 (e.g., a geometry of polysilicon of the heating elements 123, 133). Additionally or alternatively, resistance of the heating elements 123, 133 can be tuned based on doping level(s) of the heating elements 123, 133. Other methods of tuning the resistances of the heating elements 123, 133 are also possible.

In another aspect, resistance of the temperature sensors 124, 134 can be tuned based on doping level(s) of the temperature sensor 124, 134. Additionally or alternatively, resistance of the temperature sensors 124, 134 can be tuned based on a silicidation process associated with the temperature sensors 124, 134. Furthermore, the temperature sensors 124, 134 and the heating elements 123, 133 can both comprise poly-silicon. In an aspect, the temperature sensors 124, 134 can be associated with a first resistance and the heating elements 123, 133 can be associated with a second resistance. In another aspect, the temperature sensors 124, 134 can comprise a first type of polysilicon and the heating elements 123, 133 can comprise a second type of polysilicon. For example, the temperature sensors 124, 134 can comprise polysilicon associated with a first resistance and the heating elements 123, 133 can comprise polysilicon associated with a second resistance that is lower than the first resistance. As such, improved in-plane temperature uniformity for the gas sensor device 100 can be achieved. In an aspect, a first portion of the respective temperature sensors 124, 134 (e.g., a center portion of the temperature sensors 124, 134) can comprise a different resistance than one or more other portions of the respective temperature sensors 124, 134 (e.g., outer portions of the temperature sensors 124, 134).

In an aspect, potentially hazardous gases can be present in certain environments under various circumstances. These environmental hazard gases can include many different gases at varying concentrations. For instance, potentially harmful environmental gases can include, but are not limited to, nitrous oxide, hydrogen sulfide, carbon monoxide, carbon dioxide, volatile organic compounds (VOCs), etc. Such gases can be harmful at varying concentrations. For example, relatively low concentrations of gases such as nitrous oxide or hydrogen sulfide may be harmful while relatively higher concentrations of carbon dioxide can be harmful.

Chemiresistor gas sensors, such as those using metal oxide methods, can sense reactive (e.g., reducing or oxidizing) gases such as hydrogen sulfide, nitrous oxide, carbon monoxide, and VOCs at high resolution, but are generally less sensitive to nonreactive or less reactive gases such as carbon dioxide or nitrogen. Further, thermal conductivity sensing has a lower resolution than chemiresistor sensing but can detect nonreactive gases such as carbon dioxide. Accordingly, various aspects described herein utilize a CMOS-integrated gas sensor with both chemiresistor and thermal conductivity sensing capability. Novel gas sensors and methods are described herein that can switch between thermal conductivity measurement and chemiresistor measurement via the same gas sensor, which in turn can result in a gas sensor device that is sensitive to a wider range of gas species at a wider range of concentrations than conventional gas sensors.

Figure 4:
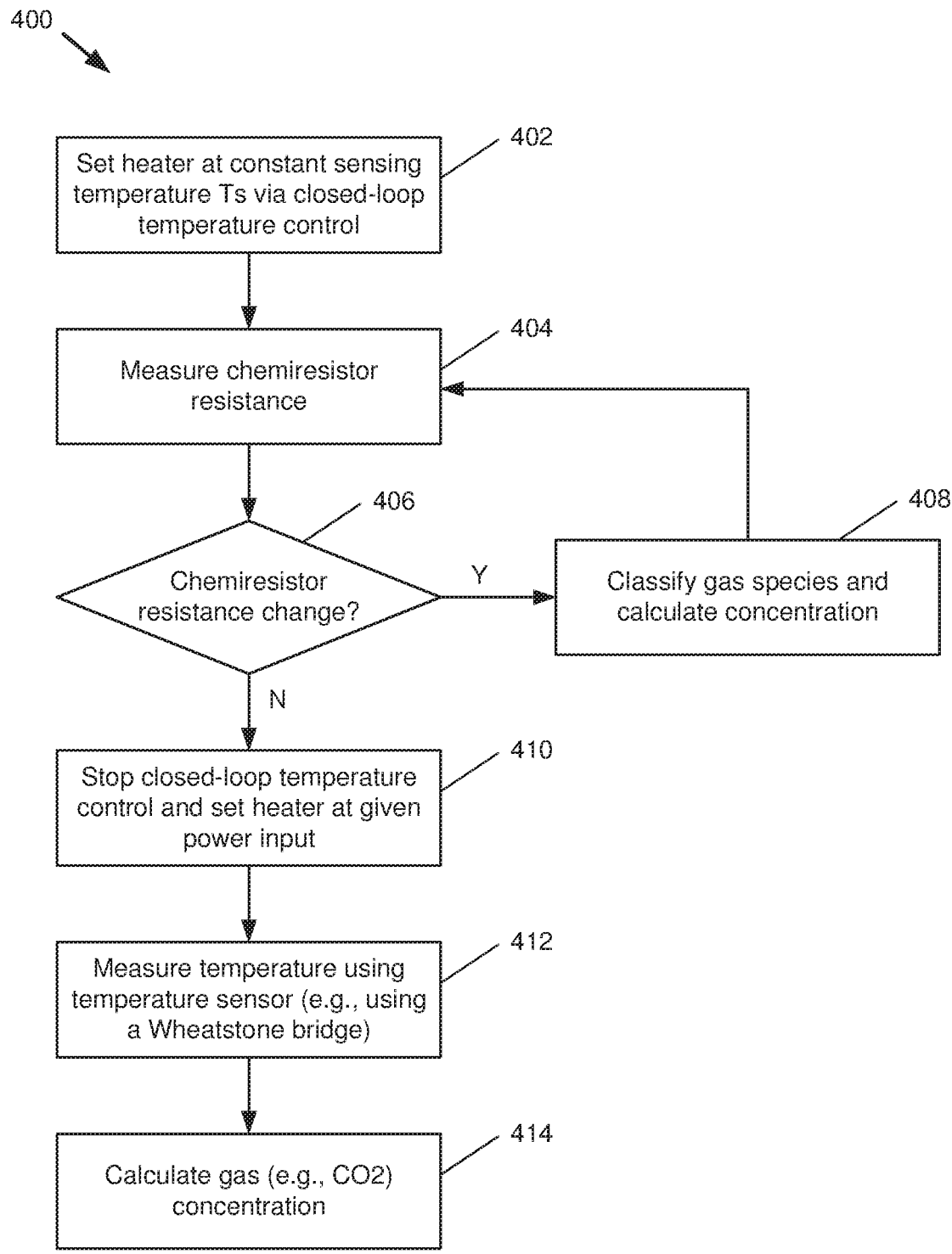
FIG. 4 is a flow diagram of a method for operating a multi-mode gas sensor in accordance with one or more embodiments of the disclosure.

FIG. 4 presents a flowchart of an example method 400 for operating a multi-mode gas sensor, e.g., a gas sensor that can operate according to a chemical sensing mode and/or a thermal sensing mode, in accordance with one or more embodiments of the disclosure. By utilizing multiple sensing techniques as described below with respect to method 400, sensing for both chemi-sensitive gases (e.g., carbon monoxide, VOCs, sulfur, etc.) and non-chemi-sensitive gases (e.g., carbon dioxide, nitrogen, etc.) can be performed via a single gas sensor. For clarity of explanation, various acts performed in connection with method 400 are described below in relation to the gas sensor 100 shown in FIG. 1. It should be appreciated, however, that method 400 can be performed using any suitable gas sensor(s).

At block 402, the heating element 123 is set to a constant sensing temperature $T_S$ via closed-loop temperature control. In one embodiment, ASIC 104 and/or other integrated circuitry is utilized to regulate the temperature of the heating element. For instance, a constant starting power level can be supplied to the heating element 123, and this power level can be adjusted (e.g., by the ASIC 104 or other controlling components) based the temperature of the heating element 123 as measured by the temperature sensor 124 and/or by other information that can be fed back directly or indirectly from the heating element 123 to the controlling components.

At block 404, the electrical resistance at a chemiresistor, e.g., chemical sensing element 121, is measured. As noted above, the chemical sensing element 121 is configured to have varying chemical and/or electrical properties in response to being exposed to one or more reactive gases in the environment surrounding the chemical sensing element 121. Here, the chemical sensing element 121 is exposed to gases in the surrounding environment via vent 127 in chamber structure 126, and the resulting change in the electrical resistance of the chemical sensing element 121, if any, is measured. To ensure consistency in the measurements performed at block 404, the heating element 123 continues to be held at the sensing temperature $T_S$ while the measurements are performed.

At block 406, the chemiresistor resistance measured at block 404 is compared to a reference electrical resistance. The reference electrical resistance can be, e.g., a previously measured resistance of the chemical sensing element 121 under fixed circumstances, a constant value, etc. In one aspect, the vent 127 of chamber structure 126 can be controllable (e.g., via a MEMS system controlled by the ASIC 104, etc.) such that the reference electrical resistance can be measured at the chemical sensing element 121 while the vent 127 is closed and the flow of environmental gases to the chemical sensing element 121 is blocked, and the measurement at block 404 can be taken upon opening the vent 127. If a change is observed between the reference electrical resistance and the resistance measured at block 404, e.g., such that a difference between said resistances is greater than a threshold or tolerance value, method 400 proceeds to block 408. Otherwise, method 400 proceeds to block 410. The operations associated with blocks 408 and 410 are described below. The tolerance value applied at block 406, if used, can be greater than or equal to zero. Thus, any change in chemiresistor resistance over the specified tolerance as observed at block 406 can cause the method 400 to branch to block 408.

At block 408, the resistance change observed at block 406 is utilized to classify the species of a gas in the environment and calculate its concentration. These operations may occur at the gas sensor 100 itself (e.g., via ASIC 104 and/or other components), or alternatively resistance measurements and/or other information collected from the gas sensor 100 can be communicated to an external computing device for further calculation. Gas classification and concentration measurement can be performed based on predefined data, e.g., a lookup table or the like that associates respective resistance measurements with gases and/or gas concentrations. Also or alternatively, machine learning and/or other artificial intelligence can be employed to train gas classifications and/or concentration measurements. In one example, based on data analysis as performed for respective sensor notes, a pattern recognition algorithm can be used to determine a present gas species. The gas species and sensor response data can then be utilized in combination with a lookup table to determine the gas concentration. Other techniques are also possible. Upon classification of environmental gases as described above, the method then returns to block 404 to perform additional sensing operations.

Alternatively, if the change in chemiresistor resistance as measured at block 406 is less than a given tolerance, the gas sensor 100 is switched from a chemical sensing mode to a thermal sensing mode. At block 410, this process begins by stopping the closed-loop temperature control initiated at block 402 and setting the heating element 123 at a given, fixed input power.

Next, at block 412, the temperature of the sensor pixel 120 is measured, e.g., by the temperature sensor 124. The temperature measured at block 412 can be a direct temperature measurement or an indirect measurement. For instance, a difference between the temperature of the sensor pixel 120 and the reference temperature provided by the TRS 130 can be measured. In an aspect, pixel 120 and TRS 130 are configured as a Wheatstone bridge such that a differential between the respective temperatures of pixel 120 and TRS 130 can be measured using the Wheatstone bridge structure. An example Wheatstone bridge that can be utilized for the measurements performed at block 412 is described below with respect to FIG. 5.

At block 414, the concentration of one or more gases in the environment surrounding the gas sensor 100 is measured based on the temperature measurements obtained at block 412. In an aspect, the calculations performed at block 412 based on temperature measurements can be performed in a similar manner to the calculations performed at block 408 based on chemiresistor resistance measurements. Also or alternatively, a gas concentration can be calculated at block 414 based on a temperature sensor response lookup table once the gas species has been classified. Upon completing the calculations associated with block 414, the method 400 can terminate, return to block 402 to resume chemiresistor sensing, or return to block 412 to resume thermal sensing.

Figure 5:
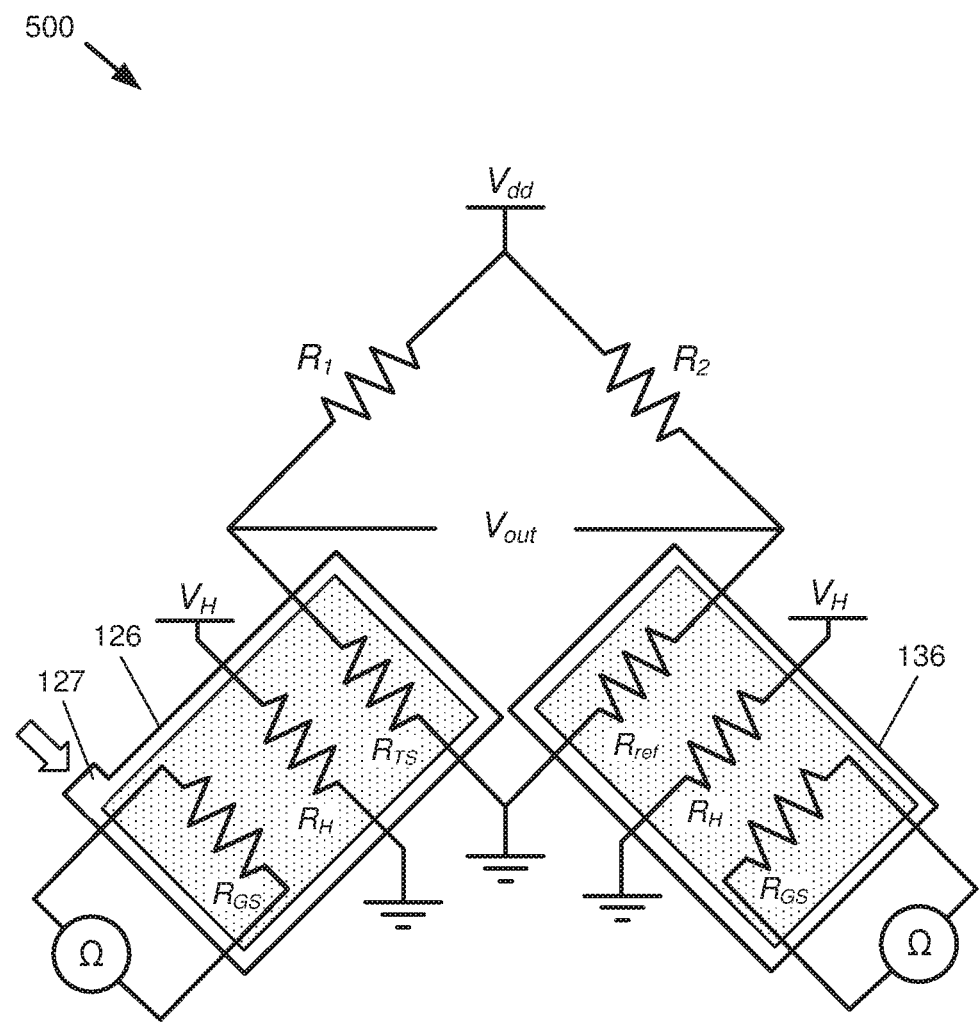
FIG. 5 is a schematic diagram depicting a Wheatstone bridge that can be utilized by the gas sensor of FIG. 1 in accordance with one or more embodiments of the disclosure.

Turning next to FIG. 5, schematic diagram 500 depicts an example Wheatstone bridge that can be utilized to perform the temperature calculations associated with thermal conductivity sensing as discussed above. The Wheatstone bridge setup shown in schematic diagram 500 is based on detection of chemiresistor changes and temperature sensor resistance changes. By utilizing the Wheatstone bridge shown in schematic diagram 500 in connection with gas sensor 100, the sensitivity of the gas sensor 100 can be increased and the drift and/or noise of the temperature sensor 124 can be reduced in the thermal conductivity measurement process.

In an aspect, the bridge heating is dominated by the heater power $V_H$ rather than $V_{dd}$. The bridge can operate on the principle that the material associated with heating element 123 is associated with a low temperature coefficient of resistance (TCR), while the material associated with temperature sensor 124 is associated with a higher TCR. Accordingly, the output voltage $V_{out}$ of the bridge will increase with a corresponding increase to the difference in thermal conductivity between an environmental gas and a reference gas employed by TRS 130.

As shown in schematic diagram 500, the two half-bridges of the gas sensor 100, e.g., pixel 120 and TRS 130, are respectively packaged into chambers 126, 136. The chamber 126 encapsulating pixel 120 contains a vent 127 such that gases from the surrounding environment can interact with pixel 120. In contrast, TRS 130 is filled with a reference gas (e.g., nitrogen and/or another inert gas) having known properties, and chamber 136 of TRS 130 forms a gas-impermeable seal between TRS 130 and the surrounding environment to prevent cross-contamination.

As TRS 130 is not exposed to outside gases, the electrical resistance $R_{TS}$ of temperature sensor 134 is used as a reference resistance $R_{ref}$ with a constant temperature. Additionally, as carbon dioxide and/or other gases enter pixel 120 via vent 127, the entering gas(es) will change the total thermal conductivity of chamber 126. As a result, the temperature of pixel 120 and chamber 126 can change based on a concentration of the gas entering pixel 120. Due to the TCR of temperature sensor 124, this change in temperature can cause the resistance $R_{TS}$ of temperature sensor 124 to change, which will cause a corresponding change in the output voltage $V_{out}$. The resulting $V_{out}$ reading can then be utilized to calculate the concentration of the gas in the environment as described above with respect to block 414 of method 400.

Figure 6:
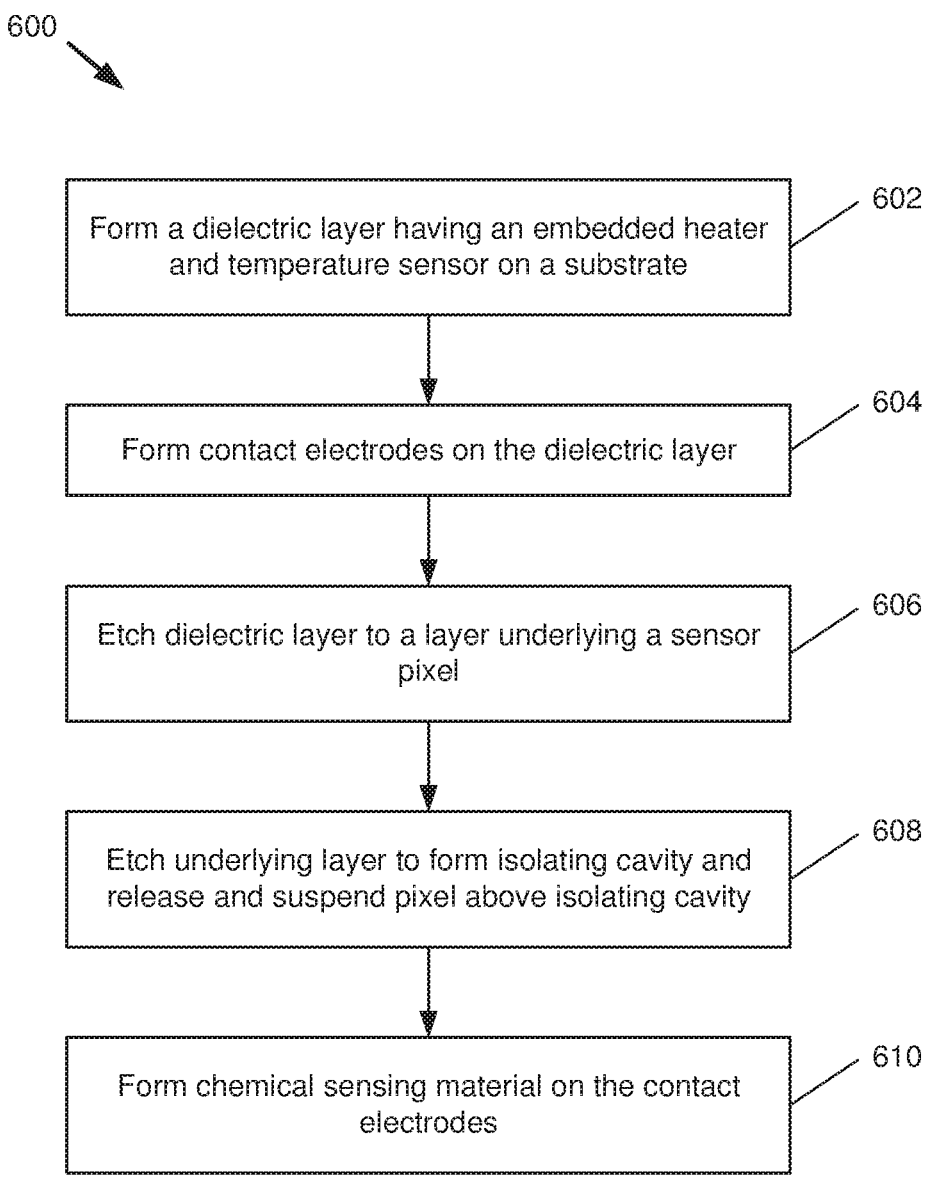
FIG. 6 is a flow diagram of a method for fabricating a structure of a gas sensor in accordance with one or more embodiments of the disclosure.

FIG. 6 presents a flowchart of an example method 600 for fabricating a gas sensor in accordance with one or more embodiments of the disclosure. At block 602, a dielectric layer is formed on a substrate. The substrate can include, for example, a semiconductor layer (e.g., a silicon slab or a silicon-on-insulator layer). A heating element, temperature sensor, and heat transfer layer are embedded in the dielectric layer. The temperature sensor is used to measure the temperature of the pixel and provide feedback for temperature control. The heating element can be formed through standard CMOS processes to for a resistive heating element, including using polysilicon, tungsten, titanium nitride, or silicon carbide. The temperature sensor may be formed from the same material and at the same time as the heating element, thereby reducing processing time and complexity. The temperature sensor is made from a material whose physical properties—such as resistance—change as a function of temperature. Other devices required by the design may also be included. For example, one or more ASIC device for controlling the heating (and thereby the operating temperature), evaluating the pixel temperature, and/or determining the gas concentration from the signals received from the pixels may be included. The ASIC may be configured to measure the electrical resistance of the chemical sensing element to determine the gas concentration in the environment.

At block 604, contact electrodes are formed on the dielectric layer. The contact electrodes are electrically connected to the chemical sensing material and are used to detect changes in the chemical sensing material as the concentration of the target gas changes. The contact electrodes can be made of conductive materials including noble metals or titanium nitride. The contact electrodes may be formed using conventional CMOS processing techniques including by sputter deposition followed by photolithographic patterning and removal of the unwanted deposited material.

At block 606, the dielectric layer is etched to the substrate or layer underlying the pixels. This etch may be done by wet etching or dry etching and it can be isotropic or anisotropic. In one example, the etching is an anisotropic etch such as deep reactive ion etching.

At block 608, the substrate or area underlying the pixels is etched to release the pixels from the bulk of the substrate or underlying layer. This etch may be done by wet etching or dry etching and it can be isotropic or anisotropic. In one example, the etching is an isotropic gas or plasma etch such as a xenon difluoride etch or a sulfur hexafluoride etch. In this etch step, a portion of the substrate or layer underneath the pixels is etched or otherwise removed to create a thermal isolation cavity that thermally isolates the pixels from the bulk of the substrate. The thermal isolation cavity allows integration of the chemical sensor with other devices (e.g., an ASIC) on the same chip. The thermal isolation cavity protects other devices on the chip from heat produced by the heating element and reduces the power consumption required to heat the pixel to the operating temperature since less heat is dissipated from the pixel to the bulk substrate. The dielectric layer provides mechanical support for the elements of the gas sensor pixel. At certain locations, the dielectric layer from the bulk of the chip is connected to the dielectric layer in the pixels. This connections provides mechanical support and allows for electrical connections to the contact electrodes, heating element, and temperature sensor.

At block 610, a chemical sensing layer is formed on the contact electrodes. The chemical sensing material may be metal oxides such as oxides of chromium, manganese, nickel, copper, tin, indium, tungsten, titanium, vanadium, iron, germanium, niobium, molybdenum, tantalum, lanthanum, cerium, and neodymium. Alternatively, the chemical sensing materials may be composite oxides including binary, ternary, quaternary and complex metal oxides. Metal oxide gas sensors are low cost and have flexibility in production, are simple to use, and have a large number of detectable gases/possible application fields. Accordingly, the metal oxide used in a specific application may be selected for sensitivities to certain chemicals. Metal oxides also function well as a chemical sensing material because they can be used to detect chemical changes through conductivity change as well as by measuring the change of capacitance, work function, mass, optical characteristics or reaction energy. The chemical sensing layer may be formed through techniques such as printing, sputter deposition, CVD, or epitaxial growth. Deposition of the chemical sensing layer may include coating the pattern of electrodes with a metal oxide compound according to a defined arrangement. This deposition, or printing, of the chemical sensing material is advantageous because it avoids problems and costs with conventional lithography and masking and can be used to form the chemical sensing structures after the pixels are released from the substrate suspended above the isolation cavity.

Figure 7:
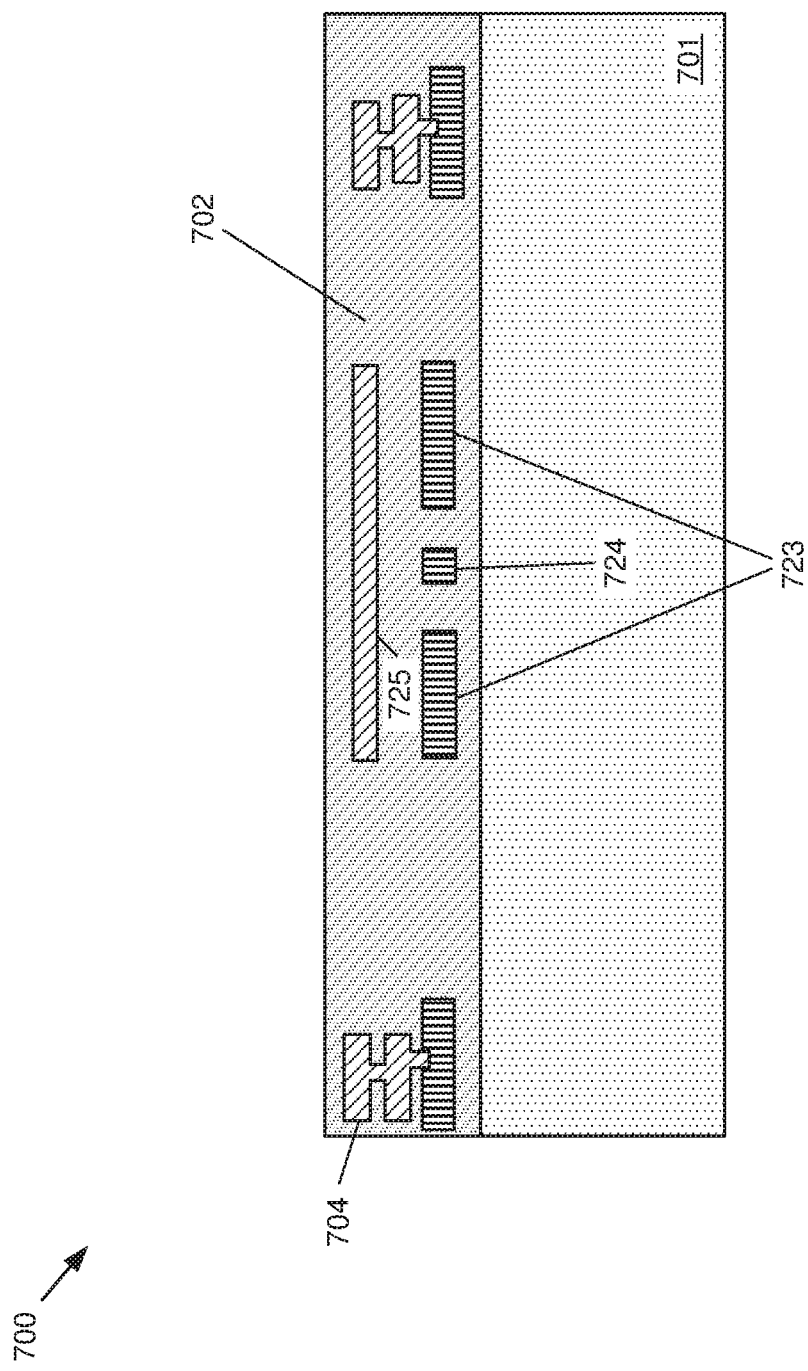
FIGS. 7-12 depict various stages of an example method for fabricating a gas sensor in accordance with one or more embodiments of the disclosure.

FIGS. 7-12 illustrate various stages of an example method for fabricating a chemical sensor in accordance with one or more embodiments of the disclosure. FIG. 7 shows a conventional CMOS wafer 700 with a dielectric layer 702 formed on a substrate 701. The substrate 701 can include, for example, a semiconductor layer (e.g., a silicon slab or a silicon-on-insulator layer). A heating element 723 is embedded in the dielectric layer. The example embodiment in FIG. 7 shows a single heating element 723, but actual devices may contain as many heating elements (and other elements described herein) as needed for the design. A temperature sensor 724 is also embedded in the dielectric layer 702. The heating element 723 can be formed through standard CMOS processes to for a resistive heating element, including using polysilicon, tungsten, titanium nitride, or silicon carbide. The temperature sensor 724 may be formed from the same material and at the same time as the heating element 723, thereby reducing processing time and complexity. The temperature sensor 724 is made from a material whose physical properties—such as resistance—change as a function of temperature. Other devices required by the desired design may also be included. For example, one or more ASIC device 704 for controlling the heating, evaluating the pixel temperature, and/or determining the concentration of chemicals from the signals received from the pixels may be included. As further shown in FIG. 7, a heat transfer or heat distribution layer 725 is also embedded in the dielectric layer 702. The heat transfer layer 725 causes the heat from the heating element 723 be more evenly distributed to the other portions of the device, including a chemical sensing layer 1121 as fabricated with respect to FIG. 11 below. In one example, the heat transfer layer 725 is a metal layer formed through standard CMOS processing.

Figure 8:
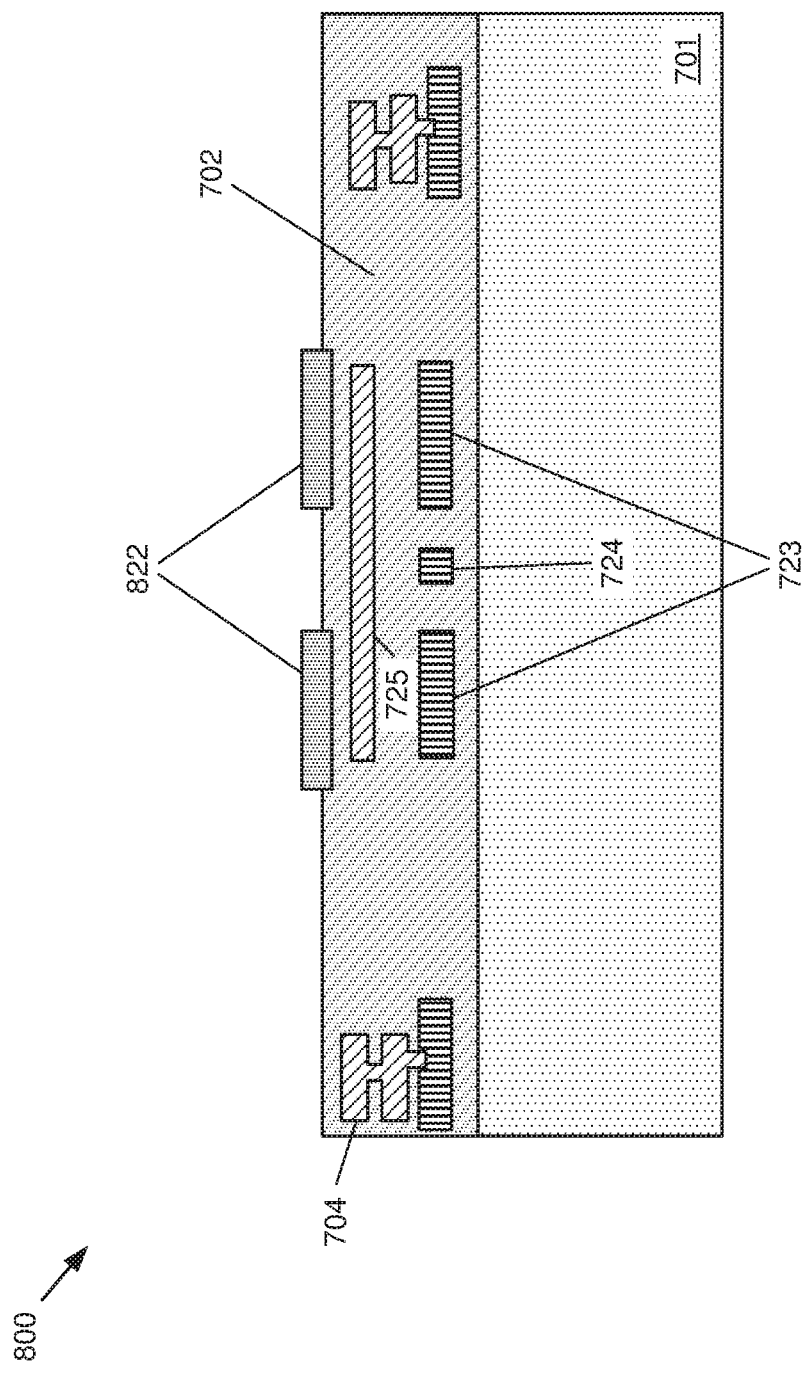

FIG. 8 shows a subsequent step in processing the wafer 700 from FIG. 7. In addition to the elements shown in FIG. 7, the wafer 800 in FIG. 8 has contact electrodes 822 that are formed on the dielectric layer 702. The contact electrodes 822 are made of conductive materials including, for example, noble metals or titanium nitride. The contact electrodes 822 may be formed using conventional CMOS processing techniques including by sputter deposition followed by photolithographic patterning and removal of the unwanted deposited material.

Figure 9:
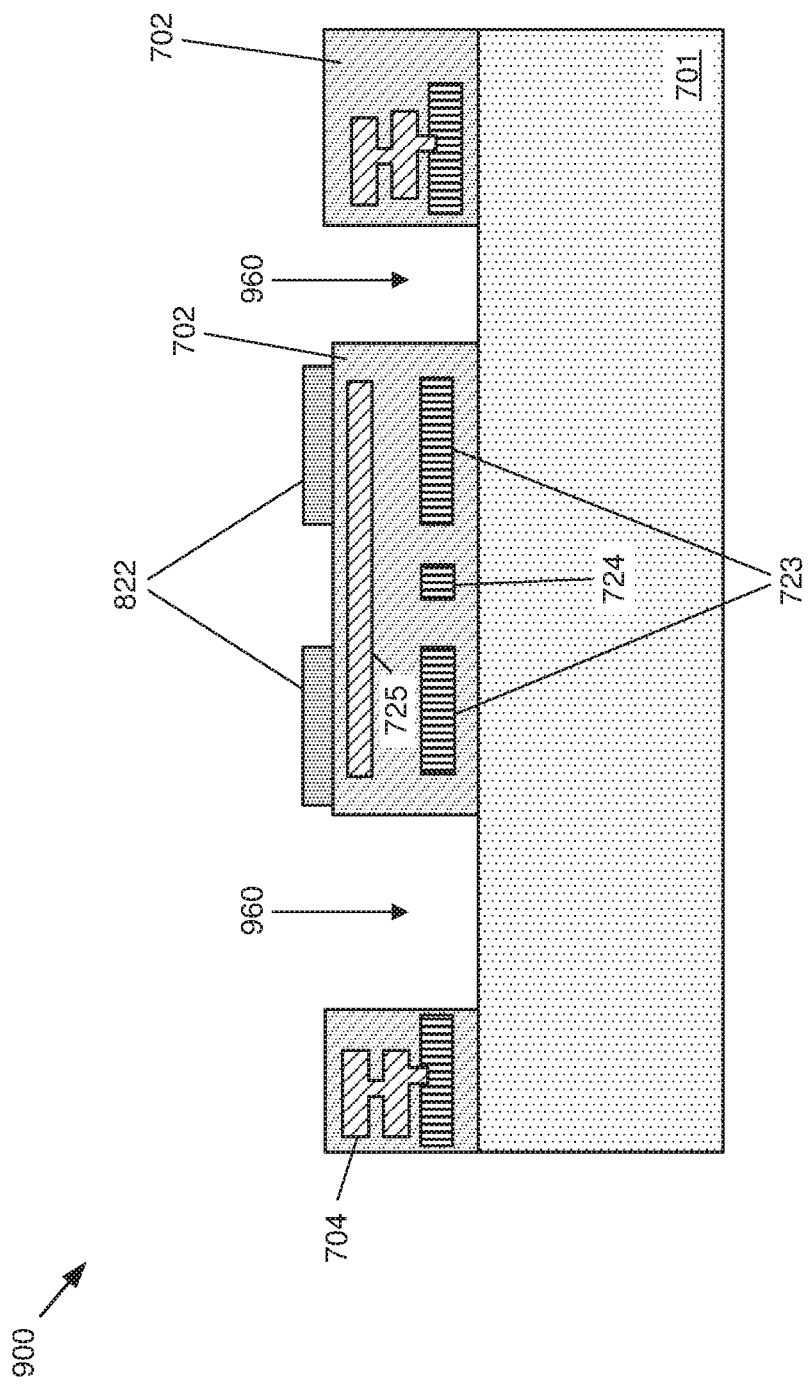

FIG. 9 shows a subsequent step in processing the wafer 800 from FIG. 8. In addition to the elements shown in FIG. 8, the wafer 900 in FIG. 9 has etched portions 980 in the dielectric layer. The etched portions 980 are etched to the substrate or layer underlying the dielectric layer 702. This etch may be done by wet etching or dry etching, and it can be isotropic or anisotropic. In a preferred method, as illustrated in FIG. 9, the etching is an anisotropic etch such as deep reactive ion etching.

Figure 10:
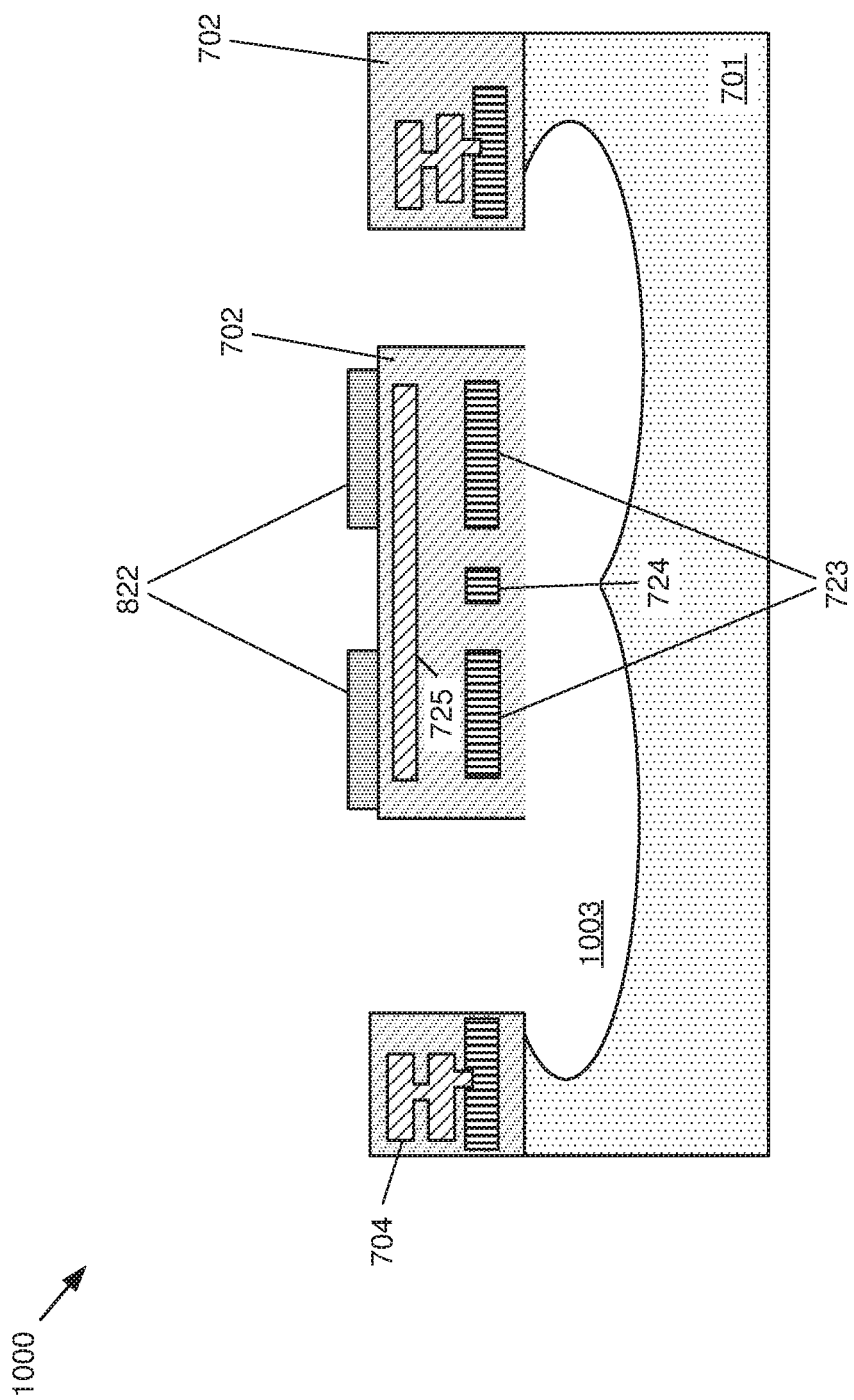

FIG. 10 shows a subsequent step in processing the wafer 900 from FIG. 9. In addition to the elements shown in FIG. 9, the wafer 1000 in FIG. 10 illustrates the formation of an isolation cavity 1003 in the substrate or area 701 underlying the dielectric layer 702. In the step shown in FIG. 10, the substrate or area 701 underlying the dielectric layer 702 is etched to release a portion of the dielectric layer 702 under the pixel area from the bulk of the substrate or underlying layer 701. This etch may be done by wet etching or dry etching, and it can be isotropic or anisotropic. In a preferred method, as shown in FIG. 10, the etching is an isotropic gas or plasma etch such as a xenon difluoride etch or a sulfur hexafluoride etch. In this etch step, a portion of the substrate or layer underneath the pixels is etched or otherwise removed to create a thermal isolation cavity 1003 that thermally isolates the pixels from the bulk of the substrate. The thermal isolation cavity 1003 allows integration of the chemical sensor with other devices (ASIC 704 for example) on the same chip. The thermal isolation cavity 1003 protects other devices on the chip from heat produced by the heating element from possible thermal damage and reduces the power consumption required to heat the pixel to the operating temperature since less heat is dissipated from the pixel to the bulk substrate. The dielectric layer 702 provides mechanical support for the elements of the gas sensor pixel. At certain locations, the dielectric layer 702 from the bulk of the chip is connected to the dielectric layer 702 in the pixels. This connection provides mechanical support and allows for electrical connections to the contact electrodes, heating element, and temperature sensor.

Figure 11:
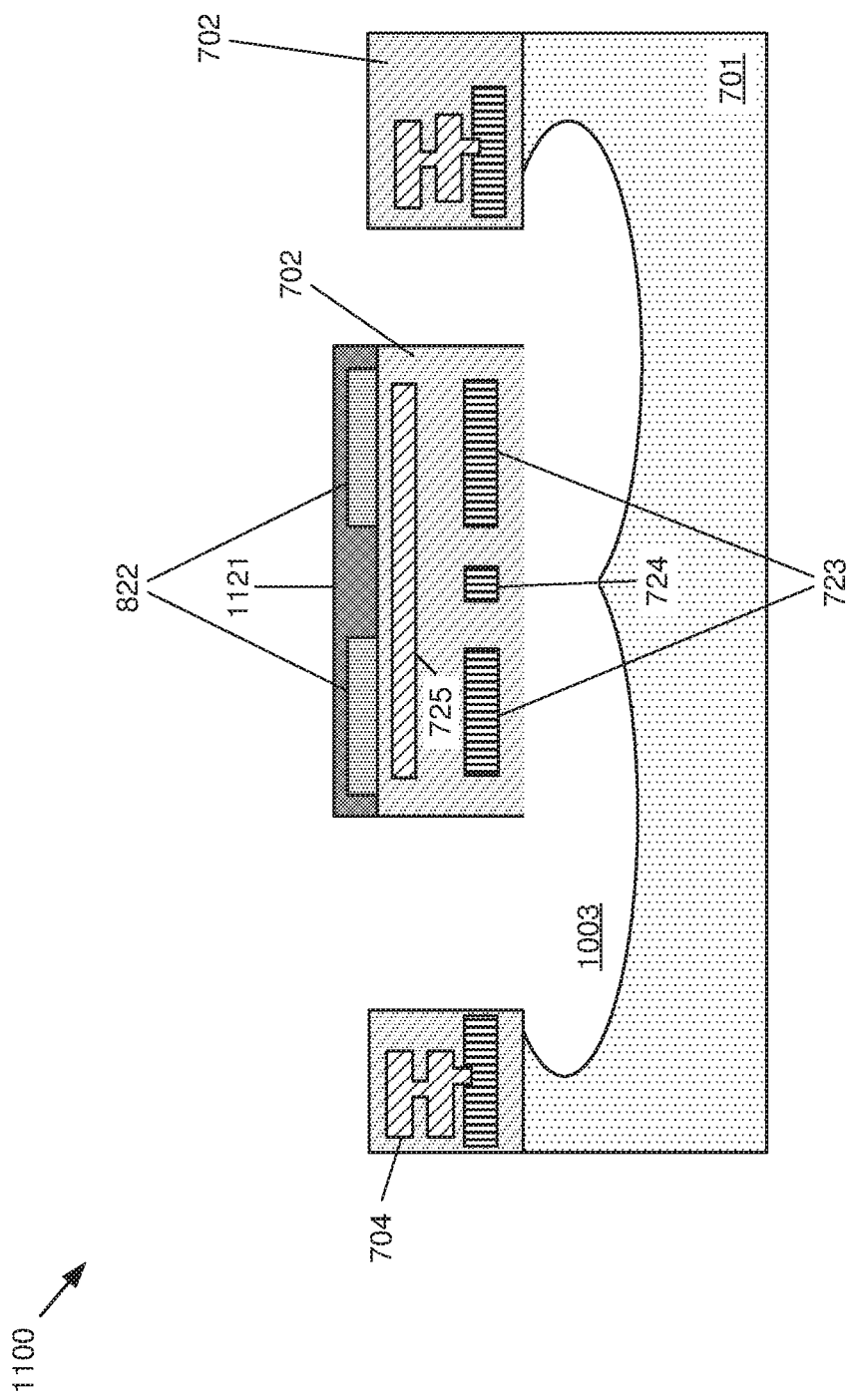

In addition to the elements shown in FIG. 10, the wafer 1100 in FIG. 11 illustrates the formation of a chemical sensing layer 1121 on the contact electrodes 822. The chemical sensing material 1121 may be composed of metal oxides such as oxides of chromium, manganese, nickel, copper, tin, indium, tungsten, titanium, vanadium, iron, germanium, niobium, molybdenum, tantalum, lanthanum, cerium, and neodymium. Alternatively, the chemical sensing material 1121 may be composed of composite oxides including binary, ternary, quaternary and complex metal oxides. Metal oxide gas sensors are low cost and have flexibility in production, are simple to use, and have a large number of detectable gases/possible application fields. Accordingly, the metal oxide used in a specific application may be selected for sensitivities to certain chemicals. Metal oxides also function well as a chemical sensing material because they can be used to detect chemical changes through conductivity change as well as by measuring the change of capacitance, work function, mass, optical characteristics or reaction energy. The chemical sensing layer may be formed through techniques such as printing, sputter deposition, CVD, or epitaxial growth. Printing the chemical sensing material may be advantageous because it avoids problems and costs with conventional lithography and masking and can be used to form the chemical sensing structures after the pixels are released from the substrate suspended above the isolation cavity. The contact electrodes 822 are electrically connected to the chemical sensing material 1121 and are used to detect changes in the chemical sensing material as the concentration of the target gas changes.

Figure 12:
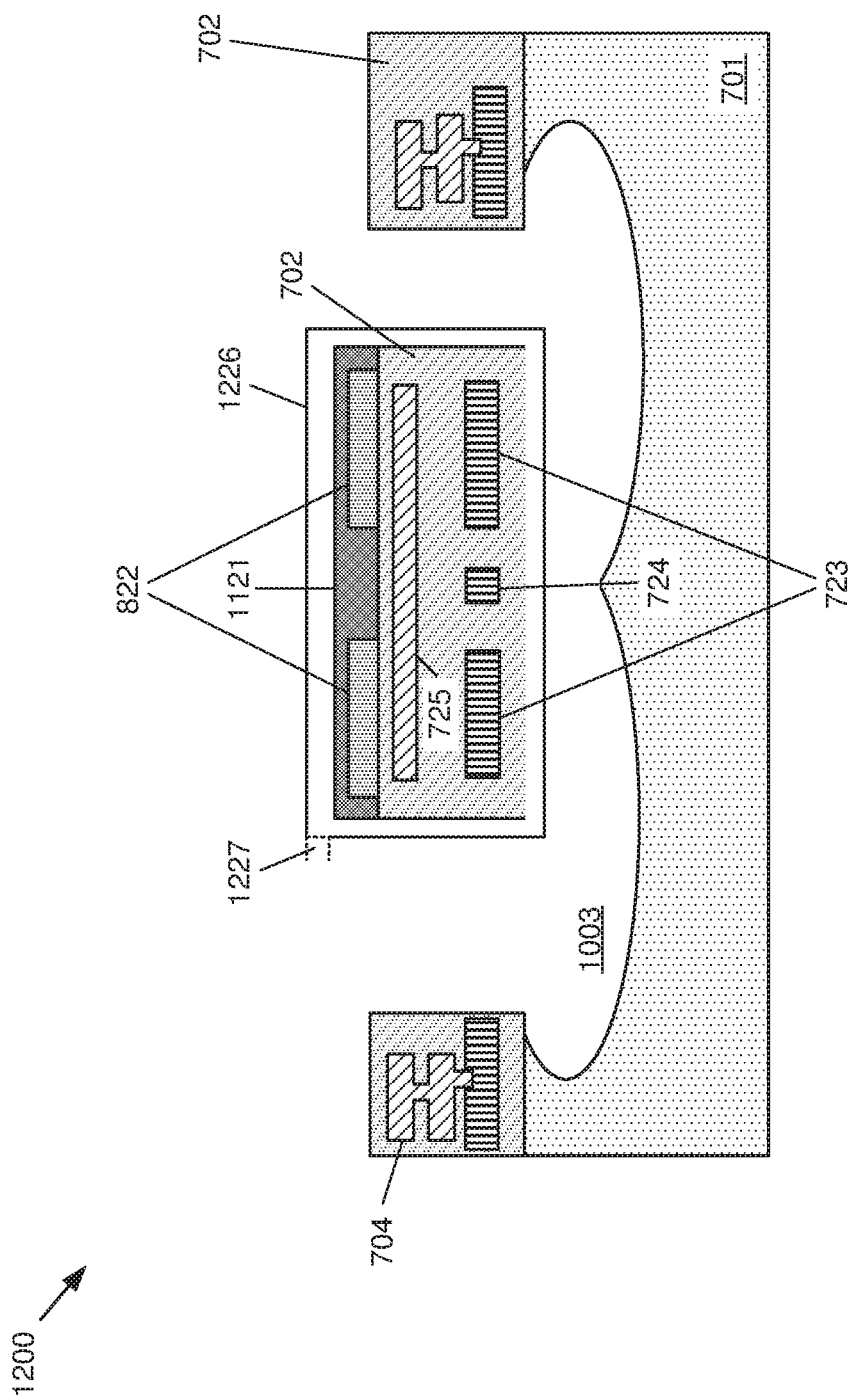

In addition to the elements shown in FIG. 11, the wafer 1200 in FIG. 12 illustrates the formation of a chamber or casing structure 1126 that encapsulates the sensor pixel. The chamber 1126 is composed of a gas-impermeable material that prevents comingling of gases inside the chamber 1126 and gases in an environment outside the chamber 1126. The chamber 1126 can optionally include a vent 1127 that enables restricted flow of gas from the environment into the pixel. The vent 1127 can be a fixed structure or controllable, e.g., such that the vent 1127 can be open at a first time and closed at a second time.

Figure 13:
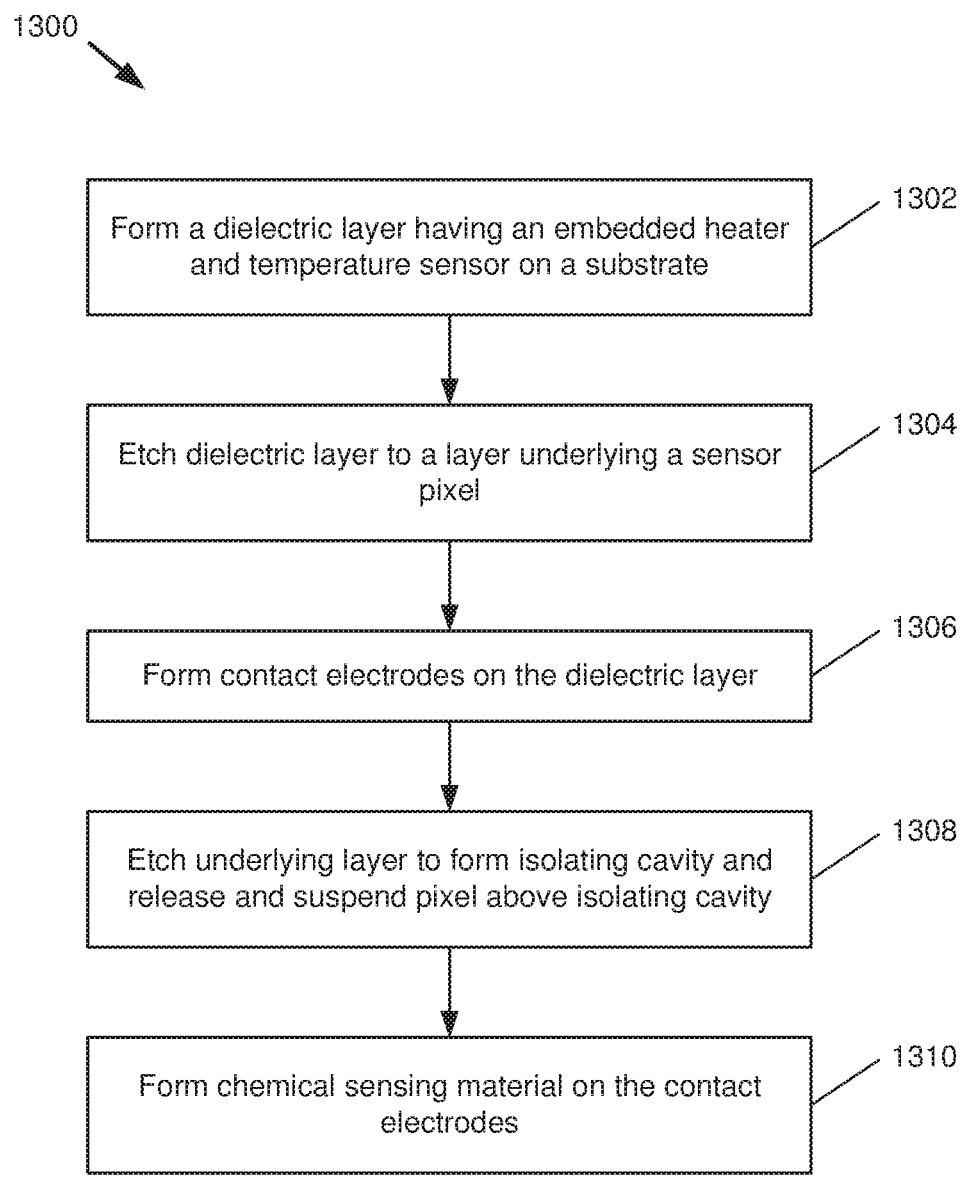
FIG. 13 is another flow diagram of a method for fabricating a structure of a gas sensor in accordance with one or more embodiments of the disclosure.

FIG. 13 presents a flowchart of another example method 1300 for fabricating a gas sensor in accordance with one or more embodiments of the disclosure. In an aspect, operations performed at the respective blocks 1302-1310 are similar to those performed at the respective blocks 602-610 shown in FIG. 6. In contrast to method 600, the dielectric layer is etched at block 1304 and contract electrodes are formed following etching of the dielectric layer at block 1306.

Figure 14:
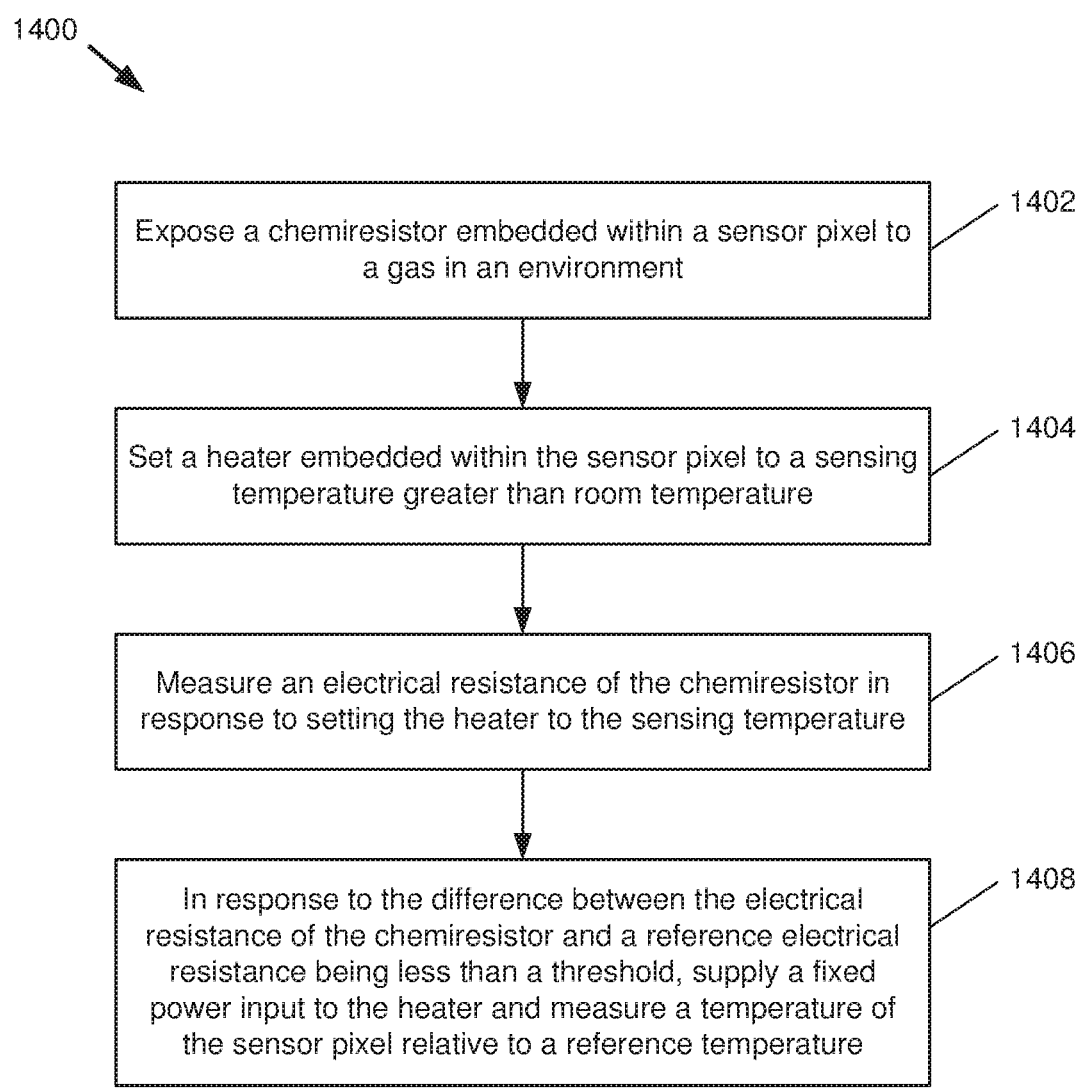
FIG. 14 is a flow diagram of a method for sensing a gas in an environment in accordance with one or more embodiments of the disclosure.

FIG. 14 presents a flowchart of an example method 1400 for sensing a gas in an environment in accordance with one or more embodiments of the disclosure. At block 1402, a chemiresistor embedded within a sensor pixel (e.g., pixel 120) is exposed to a gas in an environment. At block 1404, a heater embedded within the sensor pixel (e.g., heating element 123) is set to a sensing temperature that is greater than room temperature. At block 1406, an electrical resistance of the chemiresistor is measured in response to setting the heater to the sensing temperature at block 1404. At block 1408, in response to the difference between the electrical resistance of the chemiresistor and a reference electrical resistance being lower than a threshold, a fixed power input is supplied to the heater and a temperature of the sensor pixel is measured relative to a reference temperature (e.g., a reference temperature associated with TRS 130).

It should be appreciated that the present disclosure is not limited with respect to the chemical sensors illustrated in the figures. Rather, discussion of a specific chemical sensors for merely for illustrative purposes.

In the present specification, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in this specification and annexed drawings should generally be construed to mean "one or more" unless specified otherwise or clear from context to be directed to a singular form.

In addition, the terms "example" and "such as" are utilized herein to mean serving as an instance or illustration. Any embodiment or design described herein as an "example" or referred to in connection with a "such as" clause is not necessarily to be construed as preferred or advantageous over other embodiments or designs. Rather, use of the terms "example" or "such as" is intended to present concepts in a concrete fashion. The terms "first," "second," "third," and so forth, as used in the claims and description, unless otherwise clear by context, is for clarity only and doesn't necessarily indicate or imply any order in time.

What has been described above includes examples of one or more embodiments of the disclosure. It is, of course, not possible to describe every conceivable combination of components or methodologies for purposes of describing these examples, and it can be recognized that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method, comprising:
    exposing a chemiresistor embedded within a sensor pixel to a gas in an environment;
    placing the sensor pixel in a chemical sensing mode in response to the exposing;
    setting a heater embedded within the sensor pixel to a sensing temperature, the sensing temperature being greater than room temperature;
    measuring an electrical resistance of the chemiresistor in response to setting the heater to the sensing temperature;
    in response to a difference between the electrical resistance of the chemiresistor and a reference electrical resistance being less than a threshold, switching the sensor pixel from the chemical sensing mode to a thermal sensing mode; and
    in response to switching the sensor pixel to the thermal sensing mode, supplying a fixed power input to the heater embedded within the sensor pixel and measuring a temperature of the sensor pixel relative to a reference temperature.

2. The method of claim 1, further comprising classifying a species of the gas in the environment based on the electrical resistance of the chemiresistor.

3. The method of claim 2, wherein the classifying comprises classifying the species of the gas in the environment based on an entry of a lookup table that corresponds to the electrical resistance of the chemiresistor.

4. The method of claim 1, further comprising classifying a concentration of the gas in the environment based on the electrical resistance of the chemiresistor.

5. The method of claim 1, further comprising:
placing the sensor pixel and a temperature reference structure in a Wheatstone bridge configuration in response to the difference between the electrical resistance of a temperature sensor embedded within the sensor pixel and the reference electrical resistance being less than the threshold; and
supplying the fixed power input to the heater embedded within the sensor pixel and a second heater embedded within the temperature reference structure in response to placing the sensor pixel and temperature reference structure in the Wheatstone bridge configuration.

6. The method of claim 5, wherein the temperature of the sensor pixel is a first temperature, and wherein the method further comprises:
measuring a second temperature of the temperature reference structure in response to supplying the fixed power input to the second heater; and
setting the reference temperature to the second temperature.

7. The method of claim 6, further comprising classifying a concentration of the gas in the environment based on the temperature of the sensor pixel relative to the reference temperature.

8. The method of claim 7, further comprising returning the heater embedded within the sensor pixel to the sensing temperature in response to the classifying the concentration of the gas in the environment being completed.

9. The method of claim 1, further comprising causing the heater to remain at the sensing temperature during the measuring the electrical resistance of the chemiresistor.

10. The method of claim 1, wherein the electrical resistance of the chemiresistor is a first electrical resistance, and wherein the method further comprises:
blocking flow of the gas in the environment to the chemiresistor;
measuring a second electrical resistance of the chemiresistor in response to the blocking; and
setting the reference electrical resistance to the second electrical resistance.

11. The method of claim 10, wherein the blocking comprises closing a vent of the sensor pixel associated with the sensor pixel, and wherein the exposing comprises opening the vent of the sensor pixel subsequent to measuring the second electrical resistance.

12. The method of claim 1, wherein setting the heater comprises setting the heater embedded within the sensor pixel to the sensing temperature via closed-loop temperature control, and wherein the method further comprises:
stopping the closed-loop temperature control in response to the sensor pixel being switched from the chemical sensing mode to the thermal sensing mode.

* * * * *